US 8,632,557 B2

(12) United States Patent
Thatcher et al.

(10) Patent No.: US 8,632,557 B2
(45) Date of Patent: *Jan. 21, 2014

(54) ROTATIONAL ATHERECTOMY DEVICE AND METHOD TO IMPROVE ABRADING EFFICIENCY

(75) Inventors: Robert J. Thatcher, Blaine, MN (US); Paul A. Koehn, Wayzata, MN (US); Joseph S. Czyscon, Plymouth, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 366 days.

This patent is subject to a terminal disclaimer.

(21) Appl. No.: 12/464,524

(22) Filed: May 12, 2009

(65) Prior Publication Data
US 2010/0292720 A1 Nov. 18, 2010

(51) Int. Cl.
*A61B 17/22* (2006.01)

(52) U.S. Cl.
USPC ........................................................ 606/159

(58) Field of Classification Search
USPC ................. 606/159, 170, 167, 180, 168, 171; 604/22
See application file for complete search history.

(56) References Cited

U.S. PATENT DOCUMENTS

| | | | |
|---|---|---|---|
| 3,937,222 A | 2/1976 | Banko | |
| 4,445,509 A | 5/1984 | Auth | |
| 4,990,134 A | 2/1991 | Auth | |
| 5,308,354 A | 5/1994 | Zacca et al. | |
| 5,312,427 A | 5/1994 | Shturman | |
| 5,356,418 A | 10/1994 | Shturman | |
| 5,632,755 A | 5/1997 | Nordgren et al. | |
| 5,665,098 A | 9/1997 | Kelly et al. | |
| 5,895,397 A * | 4/1999 | Jang et al. | 606/159 |
| 6,132,444 A | 10/2000 | Shturman et al. | |
| 6,270,509 B1 * | 8/2001 | Barry et al. | 606/159 |
| 6,494,890 B1 * | 12/2002 | Shturman et al. | 606/159 |
| 6,503,261 B1 | 1/2003 | Bruneau et al. | |
| 6,565,588 B1 | 5/2003 | Clement et al. | |
| 6,572,630 B1 | 6/2003 | McGuckin, Jr. et al. | |
| 6,579,299 B2 | 6/2003 | McGuckin, Jr. et al. | |
| 6,818,001 B2 | 11/2004 | Wulfman et al. | |
| 2002/0007190 A1 | 1/2002 | Wulfman et al. | |
| 2003/0125756 A1 | 7/2003 | Shturman et al. | |
| 2004/0006358 A1 | 1/2004 | Wulfman et al. | |
| 2005/0123363 A1 | 6/2005 | Ahrnkiel et al. | |

(Continued)

OTHER PUBLICATIONS

SGS, Solid Carbide Tools, Bur Catalog. Mar. 2007 [retrieved on Apr. 5, 2010]. Retrieved from the internet: >URL: http://www.sgstool.com/catalogs/PDFs/BurCtlg.zip>.

*Primary Examiner* — S. Thomas Hughes
*Assistant Examiner* — Tin Nguyen
(74) *Attorney, Agent, or Firm* — Winthrop & Weinstine, P.A.

(57) ABSTRACT

The invention provides a rotational atherectomy system, device and method having, in various embodiments, a flexible, elongated, rotatable drive shaft with at least one eccentric abrading head attached thereto, wherein the abrading head comprises at least one groove thereon. The eccentric grooved abrading comprises a tissue removing surface—typically an abrasive surface and/or at least one groove. Preferably the eccentric enlarged abrading head has a center of mass spaced radially from the rotational axis of the drive shaft, facilitating the ability of the device to open the stenotic lesion to a diameter substantially larger than the outer diameter of the enlarged abrading head when operated at high speeds. The groove(s) provide improved efficacy in the abrasion of non-calcified and/or soft tissue as well as provide a means for breaking the hydraulic wedge between the abrading head and the stenotic tissue.

15 Claims, 10 Drawing Sheets

(56) References Cited

U.S. PATENT DOCUMENTS

| | | |
|---|---|---|
| 2005/0149083 A1 | 7/2005 | Prudnikov et al. |
| 2005/0149084 A1 * | 7/2005 | Kanz et al. .................. 606/159 |
| 2008/0103516 A1 | 5/2008 | Wulfman et al. |
| 2008/0132929 A1 | 6/2008 | O'Sullivan et al. |
| 2008/0154293 A1 | 6/2008 | Taylor |
| 2008/0306498 A1 * | 12/2008 | Thatcher et al. .............. 606/159 |

\* cited by examiner

ROTATIONAL ATHERECTOMY DEVICE AND METHOD TO IMPROVE ABRADING EFFICIENCY

BACKGROUND OF THE INVENTION

1. Field of the Invention

The invention relates to systems, devices and methods for removing tissue from body passageways, such as removal of atherosclerotic plaque from arteries, utilizing a high-speed rotational atherectomy device.

2. Description of the Related Art

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patentcy of the opened artery. For non-calcified lesions, balloon angioplasty most often is used alone to open the artery, and stents often are placed to maintain patentcy of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patentcy of the artery.

Several kinds of rotational atherectomy devices have been developed for attempting to remove stenotic material. In one type of device, such as that shown in U.S. Pat. No. 4,990,134 (Auth), a burr covered with an abrasive abrading material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently more than one size burr must be utilized to open an artery to the desired diameter.

U.S. Pat. No. 5,314,438 (Shturman) discloses another atherectomy device having a drive shaft with a section of the drive shaft having an enlarged diameter, at least a segment of this enlarged surface being covered with an abrasive material to define an abrasive segment of the drive shaft. When rotated at high speeds, the abrasive segment is capable of removing stenotic tissue from an artery. Though this atherectomy device possesses certain advantages over the Auth device due to its flexibility, it also is capable only of opening an artery to a diameter about equal to the diameter of the enlarged abrading surface of the drive shaft since the device is not eccentric in nature.

U.S. Pat. No. 6,494,890 (Shturman) discloses an atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. Since the enlarged eccentric section comprises drive shaft wires that are not bound together, the enlarged eccentric section of the drive shaft may flex during placement within the stenosis or during high speed operation. This flexion allows for a larger diameter opening during high speed operation, but may also provide less control than desired over the diameter of the artery actually abraded. In addition, some stenotic tissue may block the passageway so completely that the Shturman device cannot be placed therethrough. Since Shturman requires that the enlarged eccentric section of the drive shaft be placed within the stenotic tissue to achieve abrasion, it will be less effective in cases where the enlarged eccentric section is prevented from moving into the stenosis. The disclosure of U.S. Pat. No. 6,494,890 is hereby incorporated by reference in its entirety.

U.S. Pat. No. 5,681,336 (Clement) provides an eccentric tissue removing burr with a coating of abrasive particles secured to a portion of its outer surface by a suitable binding material. This construction is limited, however because, as Clement explains at Col. 3, lines 53-55, that the asymmetrical burr is rotated at "lower speeds than are used with high speed ablation devices, to compensate for heat or imbalance." That is, given both the size and mass of the solid burr, it is infeasible to rotate the burr at the high speeds used during atherectomy procedures, i.e., 20,000-200,000 rpm. Essentially, the center of mass offset from the rotational axis of the drive shaft would result in development of significant centrifugal force, exerting too much pressure on the wall of the artery and creating too much heat and excessively large particles.

In general, current tissue-removing elements comprise continuous abrasive surfaces in e.g., either a symmetrical or asymmetrical elliptical or spherical configuration. It is known that a hydraulic wedge forms in some cases between the current tissue-removing element design and the arterial wall and plaque, reducing the contact between the abrasive and the plaque and, as a result, reducing the efficacy of the procedure. Moreover, the relatively smooth abrasive face of current designs does not maximize abrading and/or cutting efficacy. Finally, the known relatively smooth tissue-removing element designs result in atherectomy procedures of unpredictable length when working with soft plaque and/or non-calcified lesions and/or diffuse lesions.

Accordingly, there exists a need for an atherectomy device having a tissue-removing element with facial grooves and comprising additional cutting edges and features as well as providing a mechanism for breaking the hydraulic wedge that exists between the abrasive and the arterial wall and plaque. In addition, a need exists for a tissue-removing element that is more effective with soft plaque and/or non-calcified and/or diffuse lesions, thereby increasing the predictability of procedure outcome and length when working with such blockages.

BRIEF SUMMARY OF THE INVENTION

The invention provides a rotational atherectomy system, device and method having, in various embodiments, a flexible, elongated, rotatable drive shaft with at least one eccentric abrading head attached thereto, wherein the abrading head comprises at least one groove thereon. The eccentric grooved abrading comprises a tissue removing surface—typically an abrasive surface and/or at least one groove. Preferably the eccentric enlarged abrading head has a center of mass spaced radially from the rotational axis of the drive shaft, facilitating the ability of the device to open the stenotic lesion to a diameter substantially larger than the outer diameter of the enlarged abrading head when operated at high speeds. The groove(s) provide improved efficacy in the abrasion of non-calcified and/or soft tissue as well as provide a means for breaking the hydraulic wedge between the abrading head and the stenotic tissue.

An object of the invention is to provide a high-speed rotational atherectomy device having at least one eccentric abrading head operatively connected to a rotatable drive shaft and having a resting diameter smaller than its high-speed rotational diameter and comprising at least one groove along the tissue removing surface.

Another object of the invention is to provide a high-speed rotational atherectomy device having at least one eccentric abrading head comprising at least one groove along the tissue removing surface of the abrading head for facilitating breaking the hydraulic wedge between the tissue removing surface and the stenotic tissue.

Another object of the invention is to provide a high-speed rotational atherectomy device having at least one eccentric abrading head comprising at least one groove along the tissue removing surface of the abrading head for improving the efficacy in abrading non-calcified and/or soft stenotic tissue.

Another object of the invention is to provide a high-speed rotational atherectomy device having at least one eccentric abrading head comprising at least one radial and/or axial groove along the tissue removing surface of the abrading head.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

Figure 1:
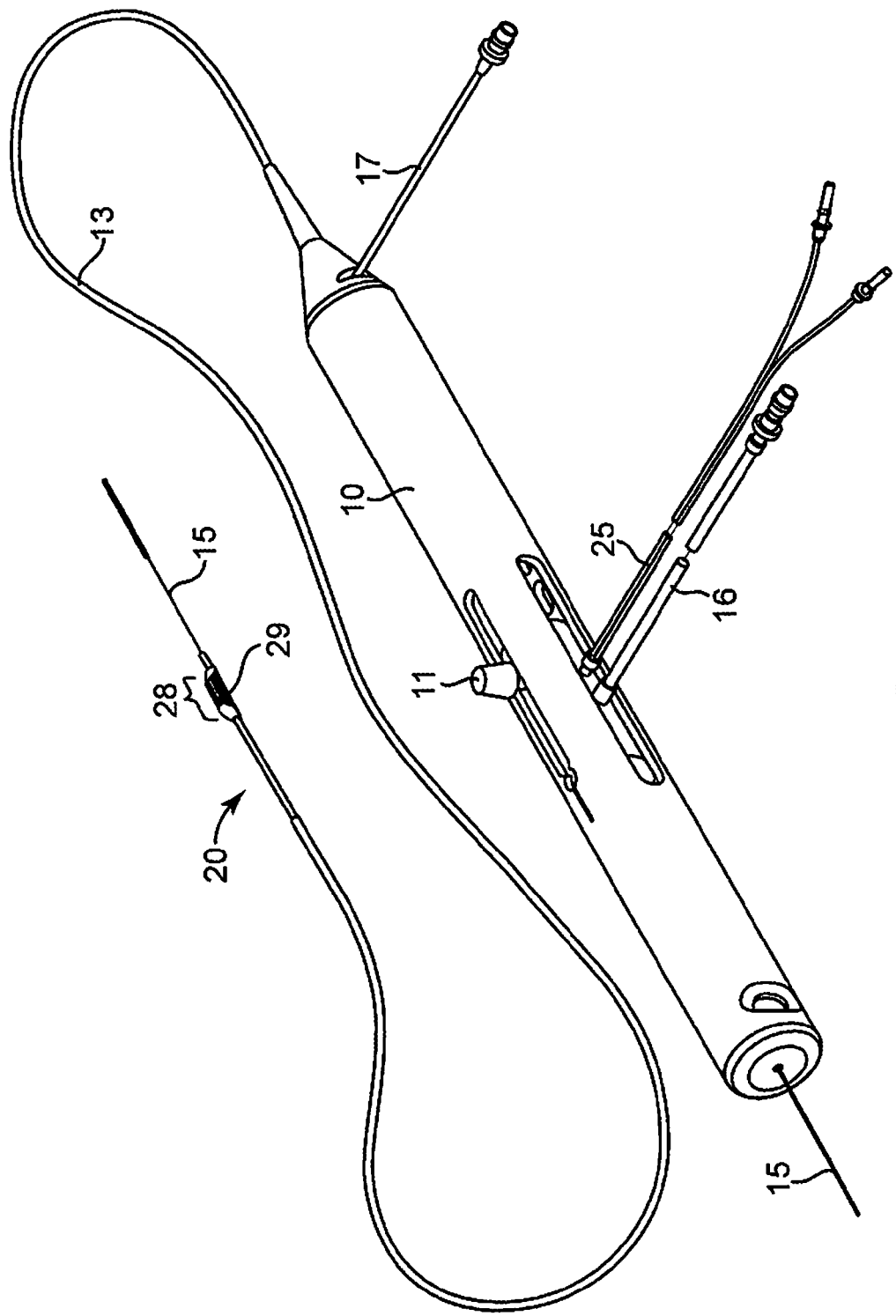
FIG. 1 is a perspective view of one embodiment of a non-flexible eccentric abrading head of a rotational atherectomy device of the invention.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

FIG. 1 illustrates one embodiment of a rotational atherectomy device according to the present invention. The device includes a handle portion 10, an elongated, flexible drive shaft 20 having an eccentric enlarged abrading head 28, the abrading head having at least one groove 29, and an elongated catheter 13 extending distally from the handle portion 10. The drive shaft 20 is constructed from helically coiled wire as is known in the art and the abrading head 28 is fixedly attached thereto. Grooves 29 are illustrated along the tissue-removing surface of abrading head 28. In the illustrated embodiment grooves 29 are axial, though other arrangements of the grooves 29 are within the scope of the present invention and are discussed further herein. The catheter 13 has a lumen in which most of the length of the drive shaft 20 is disposed, except for the enlarged abrading head 28 and a short section distal to the enlarged abrading head 28. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 25, alternatively a single fiber optic cable may be used, may also be provided for monitoring the speed of rotation of the turbine and drive shaft 20 (details regarding such handles and associated instrumentation are well know in the industry, and are described, e.g., in U.S. Pat. No. 5,314,407, issued to Auth). The handle 10 also desirably includes a control knob 11 for advancing and retracting the turbine and drive shaft 20 with respect to the catheter 13 and the body of the handle.

Figure 2:
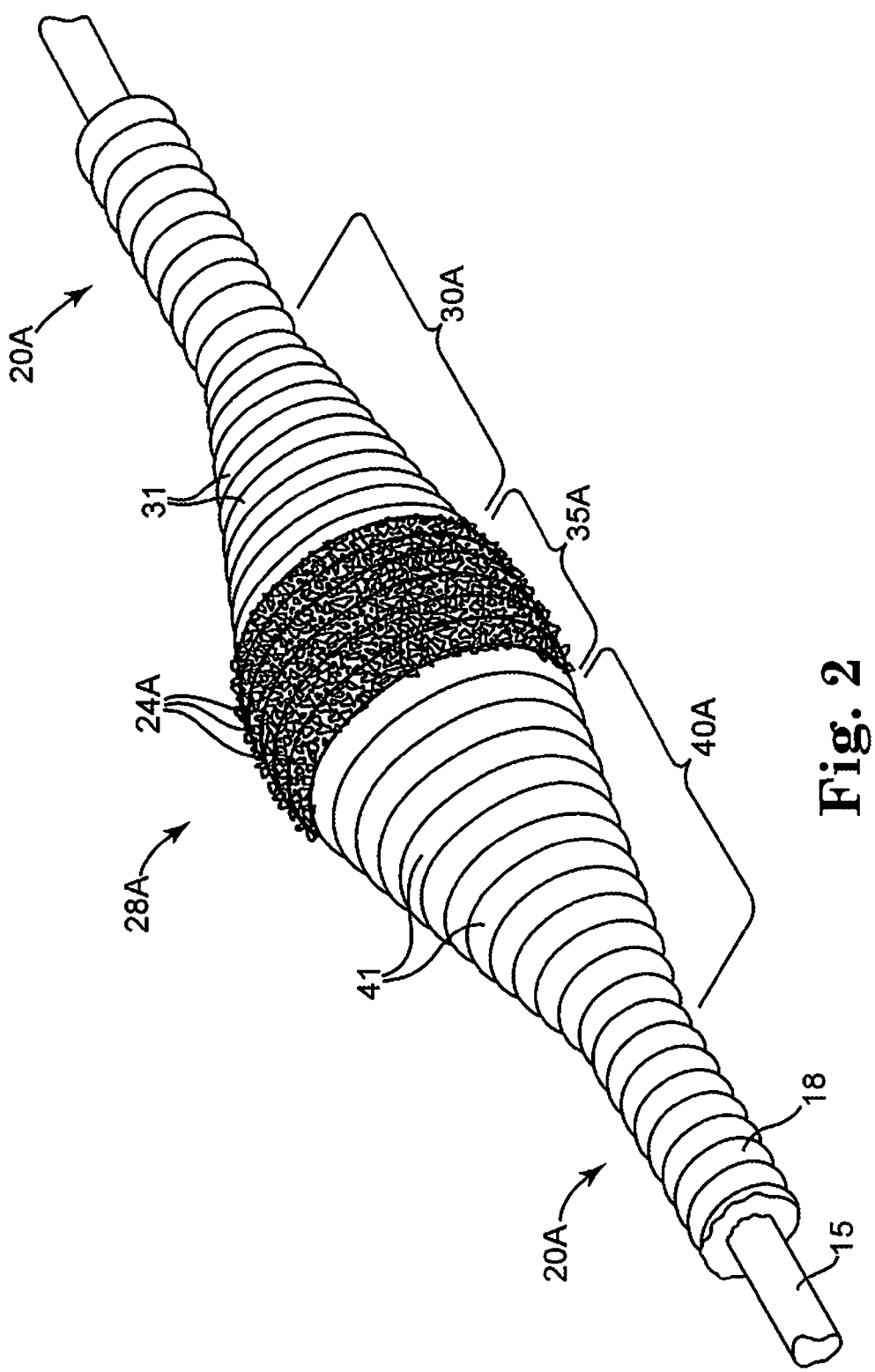
FIG. 2 is perspective, broken-away view of a prior art abrading head formed from wire turns of a rotatable drive shaft.
Figure 3:
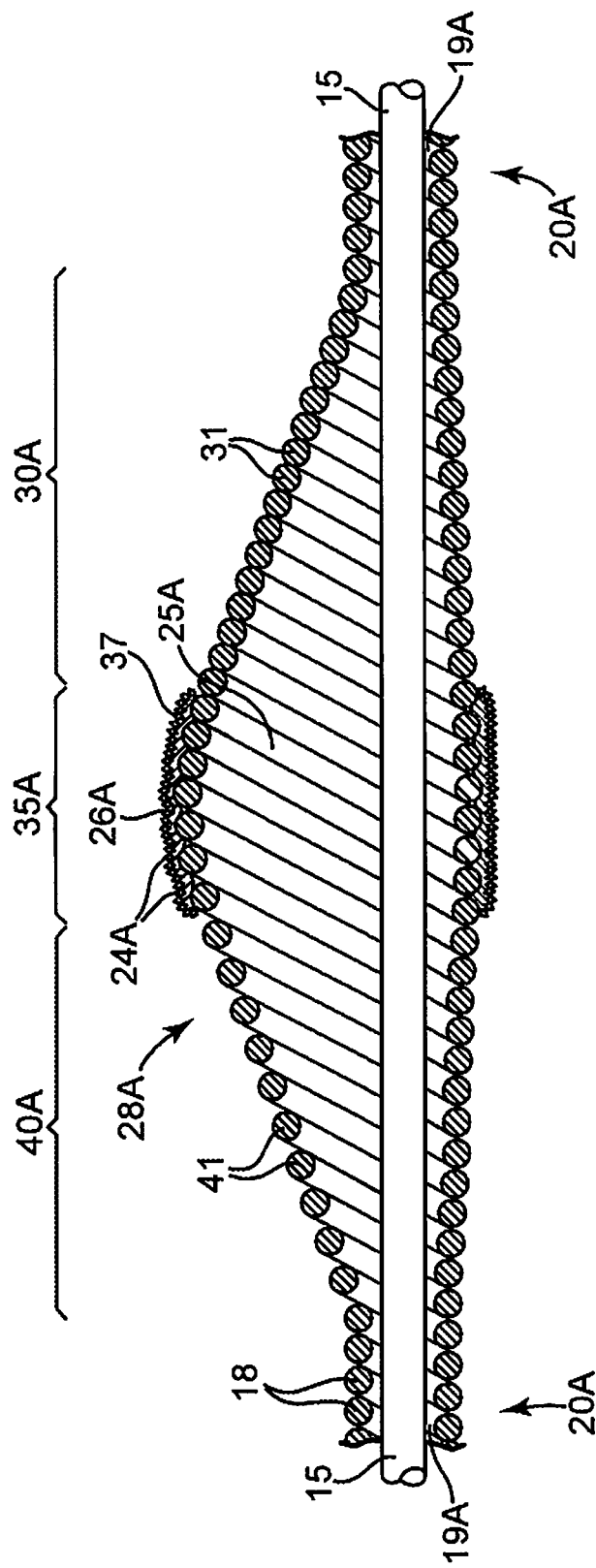
FIG. 3 is a broken-away, longitudinal cross-sectional view of a prior art eccentric abrading head formed from the wire turns of a rotatable drive shaft.

FIGS. 2 and 3 illustrate details of a prior art abrading head comprising an eccentric enlarged diameter abrading section 28A of a drive shaft 20A. The drive shaft 20A comprises one or more helically wound wires 18 which define a guide wire lumen 19A and a hollow cavity 25A within the enlarged abrading section 28A. Except for the guide wire 15 traversing the hollow cavity 25A, the hollow cavity 25A is substantially empty. The eccentric enlarged diameter abrading section 28A includes, relative to the location of the stenosis, proximal 30A, intermediate 35A and distal 40A portions. Wire turns 31 of the proximal portion 30A of the eccentric enlarged diameter section 28A preferably have diameters that progressively increase distally at a generally constant rate, thereby forming generally the shape of a cone. Wire turns 41 of the distal portion 40A preferably have diameters that progressively decrease distally at a generally constant rate, thereby forming generally the shape of a cone. Wire turns 36 of the intermediate portion 35A are provided with gradually changing diameters to provide a generally convex outer surface which is shaped to provide a smooth transition between the proximal and distal conical portions of the enlarged eccentric diameter section 28A of the drive shaft 20A.

Continuing with the prior art device, at least part of the eccentric enlarged diameter abrading section of the drive shaft 28A (preferably the intermediate portion 35A) comprises an external surface capable of removing tissue. A tissue removing surface 37 comprising a coating of an abrasive material 24A to define a tissue removing segment of the drive shaft 20A is shown attached directly to the wire turns of the drive shaft 20A by a suitable binder 26A.

Figure 4:
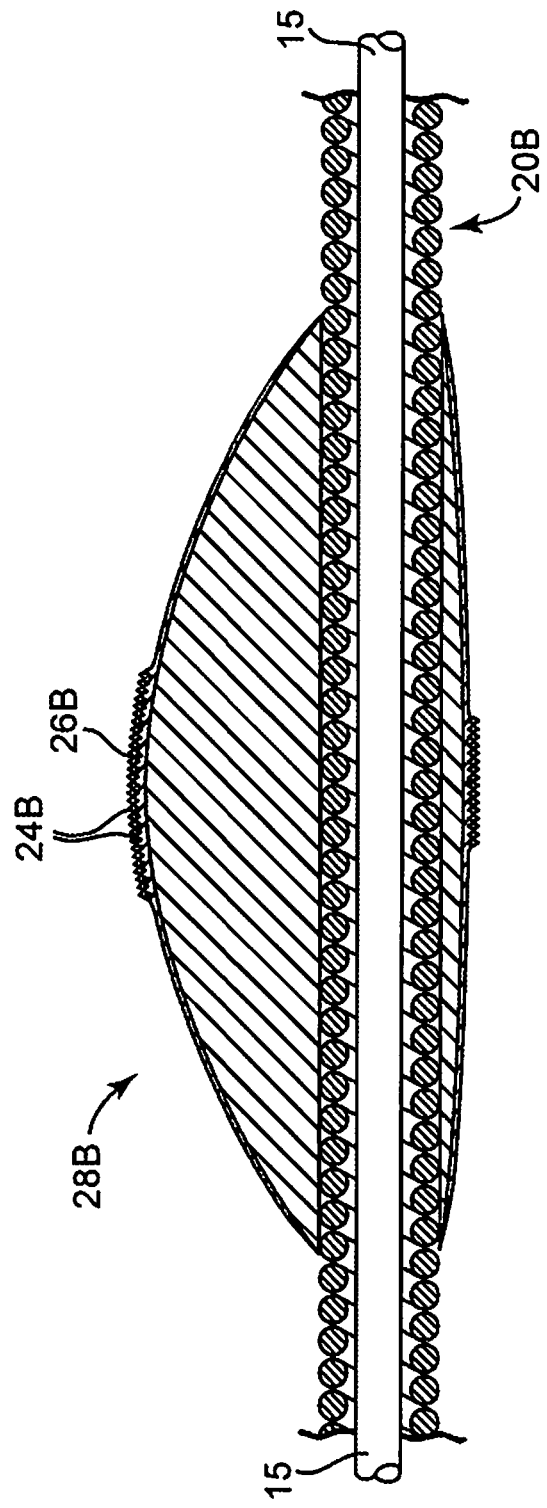
FIG. 4 is a broken away, longitudinal cross-sectional view of a prior art solid eccentric burr.

FIG. 4 illustrates another prior art rotational atherectomy device which, in contrast with the substantially hollow device of FIGS. 2 and 3, employs a solid asymmetrical abrasive burr 28B attached to a flexible drive shaft 20B, rotated over a guide wire 15 such as provided by U.S. Pat. No. 5,681,336 to Clement. The eccentric tissue removing burr 28B has a coating of abrasive particles 24B secured to a portion of its outer surface by a suitable binding material 26B. This construction has limited utility, however because, as Clement explains at Col. 3, lines 53-55, the asymmetrical burr 28B must be rotated at "lower speeds than are used with high speed ablation devices, to compensate for heat or imbalance." That is, given both the size and mass of the solid burr-type construction, it is infeasible to rotate such a burr at the high speeds used during atherectomy procedures, i.e., 20,000-200,000 rpm. Further, the abrasive section of this prior art device is relatively smooth, i.e., grooves are not present. As a result, this prior art device will be less than efficient when dealing with non-calcified and/or soft stenoses.

Turning now to FIGS. 5 and 6A-6C, one embodiment of the present invention is illustrated. The abrading head 28 comprises three sections: a cone-shaped distal section 30, a cylindrical-shaped intermediate section 35 and a cone-shaped proximal section 40. Thus, the proximal section 40 comprises a proximal outer surface, the intermediate section comprises an intermediate outer surface and the distal section 30 comprises a distal outer surface, the proximal outer surface having diameters that increase distally, the distal outer surface having diameters that decrease distally, and the intermediate outer surface being cylindrical. As illustrated, the intermediate section 35 comprises axial grooves 29. The present invention may comprise at least one such groove 29 disposed on the outer surface of at least the intermediate section 35. The outer surface of the intermediate section 35 further comprises non-grooved sections 31 between each groove 29.

A preferred embodiment comprises the at least one groove 29 located within the intermediate section 35, though the distal 30 and/or proximal 40 sections may comprise at least one groove 29 in alternate embodiments. The groove(s) 29 aid in the abrading, cutting and/or grinding of soft and/or non-calcified tissue or plaque from the vessel. In one aspect, the groove(s) 29 provide a mechanism and a method for disrupting or breaking the hydraulic wedge that typically results when a relatively smooth surfaced abrasive head rotates at high speed against the stenosis and/or arterial wall. The groove(s) 29 thus provides increased contact between the abrasive head 28 and the stenosis and, as a result, improves abrasive efficiency and efficacy. In a second aspect, the groove(s) 29 provide a mechanism and a method for abrading, cutting and/or grinding non-calcified and/or soft tissue by allowing the soft tissue to expand slightly into the groove, rendering this tissue more amenable to abrasion, cutting and/or grinding, i.e., removal by the rapidly rotating abrading head 28. This is similar to the use of multiple, parallel blades on a razor; a hair portion left behind by a first blade may "spring up" and be cut by one or more subsequent blades. In a third aspect, the groove(s) 29 provide a pathway allowing abraded, removed material to flow away from the cutting area. In various embodiments, the number of groove(s) 29 may be one or more, i.e., two, three, four, five, six or any suitable number.

Figure 5:
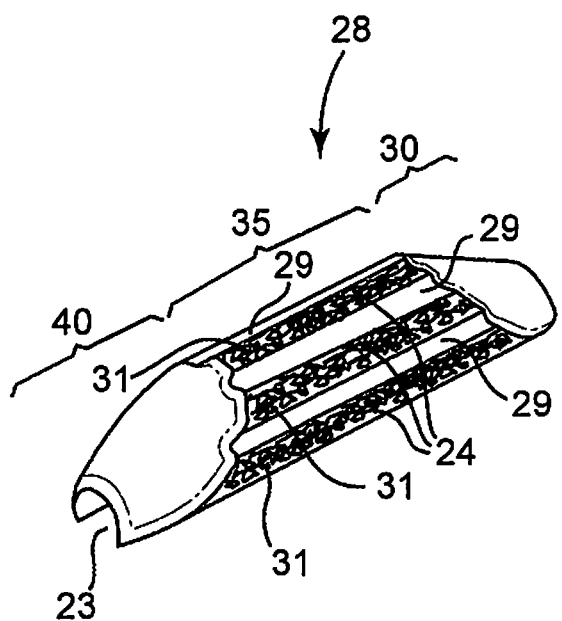
FIG. 5 is a perspective view of one embodiment of an abrading head of the present invention.
Figure 6A:
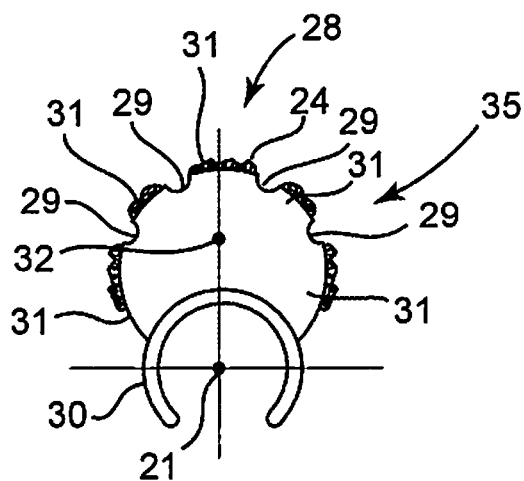
FIG. 6A is a front view of one embodiment of an abrading head of the present invention.

The abrading head 28 may further comprise at least one tissue removing surface disposed on the external surface(s) of the intermediate section 35, the distal section 30 and/or the proximal section 40 to facilitate abrasion of the stenosis during high speed rotation. The tissue removing surface may comprise a coating of an abrasive material 24 bound to the external surface(s) of the intermediate section 35, the distal section 30 and/or the proximal section 40 of abrading head 28. As illustrated in FIGS. 5 and 6A, the abrasive material 24 may be bound to the non-grooved sections 31 located between each groove 29. Alternate embodiments may comprise the abrasive material 24 being further bound within the groove(s) 29. In all embodiments of abrading head 28 discussed herein and the equivalents thereof, the at least one groove 29 may be curved in profile or may have a non-curvilinear profile, i.e., a flute shape as is well known to the skilled artisan.

As is well understood in the art, the abrasive material may be any suitable material, such as diamond powder, fused silica, titanium nitride, tungsten carbide, aluminum oxide, boron carbide, or other ceramic materials. Preferably the abrasive material is comprised of diamond chips (or diamond dust particles) attached directly to the tissue removing surface(s) by a suitable binder. Such attachment may be achieved using well known techniques, such as conventional electroplating or fusion technologies (see, e.g., U.S. Pat. No. 4,018,576). Alternately the external tissue removing surface may comprise mechanically or chemically roughening the external surface(s) of the intermediate portion 35, the distal portion 40 and/or the proximal portion 30 to provide a suitable abrasive tissue removing surface. In yet another variation, the external surface may be etched or cut (e.g., with a laser) to provide small but effective abrading surfaces. Other similar techniques may also be utilized to provide a suitable tissue removing surface.

Figures 6B, 6C:
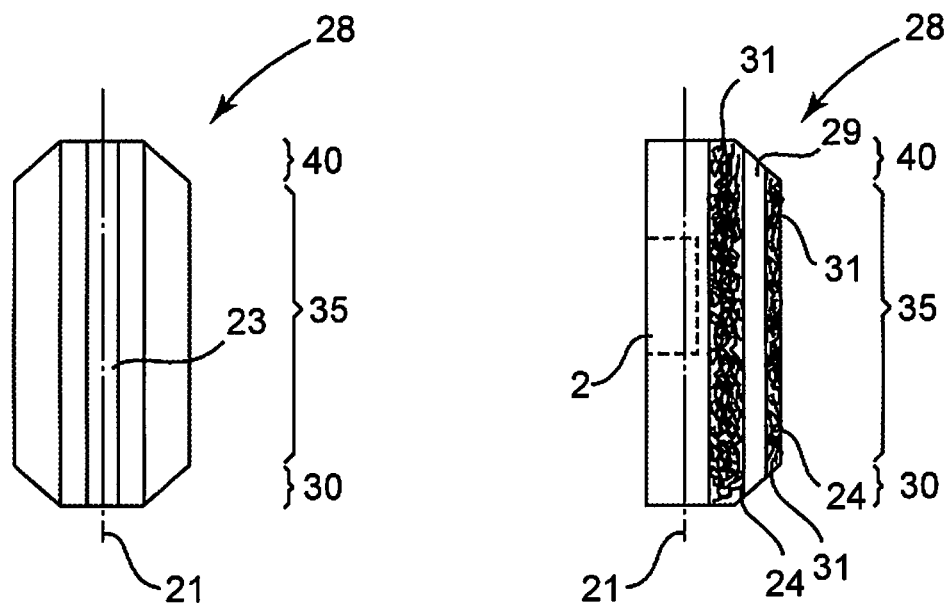
FIG. 6B is a bottom view of one embodiment of an abrading head of the present invention.
FIG. 6C is a side view of one embodiment of an abrading head of the present invention.
Figure 7A:
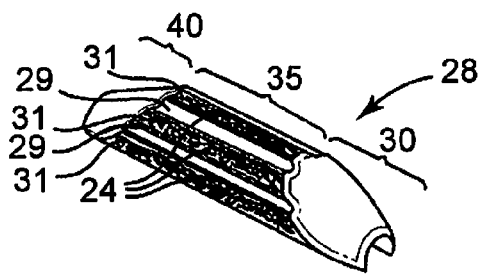
FIG. 7A is a perspective view of one embodiment of an abrading head of the present invention.
Figure 7B:
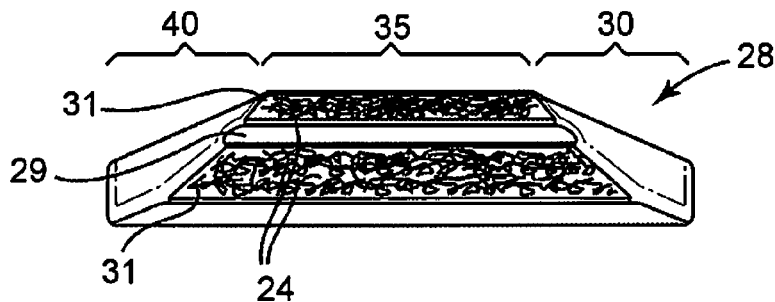
FIG. 7B is a side view of one embodiment of an abrading head of the present invention.
Figure 7C:
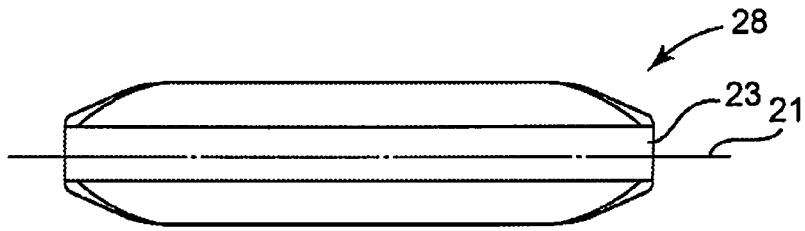
FIG. 7C is a bottom view of one embodiment of an abrading head of the present invention.
Figure 7D:
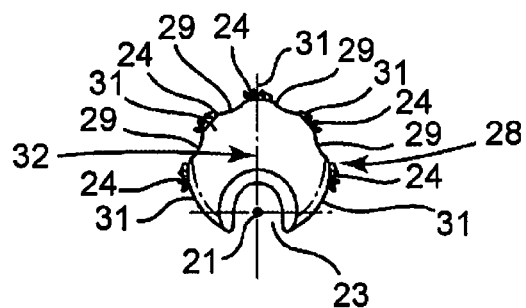
FIG. 7D is a front view of one embodiment of an abrading head of the present invention.
Figure 8A:
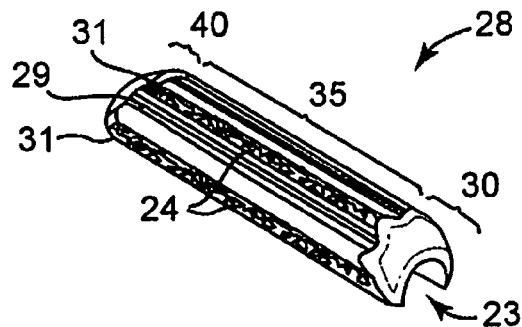
FIG. 8A is a perspective view of one embodiment of an abrading head of the present invention.
Figure 8B:
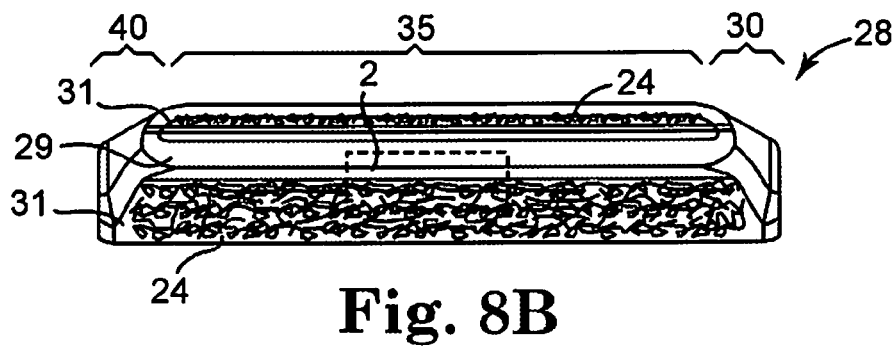
FIG. 8B is a side view of one embodiment of an abrading head of the present invention.
Figure 8C:
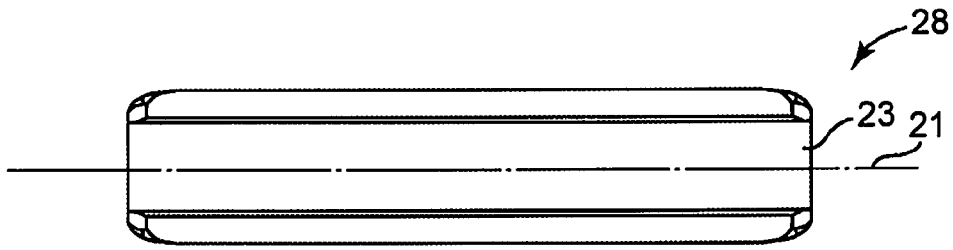
FIG. 8C is a bottom view of one embodiment of an abrading head of the present invention.
Figure 8D:
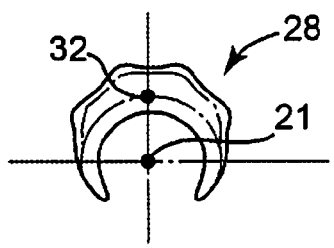
FIG. 8D is a front view of one embodiment of an abrading head of the present invention.
Figure 9A:
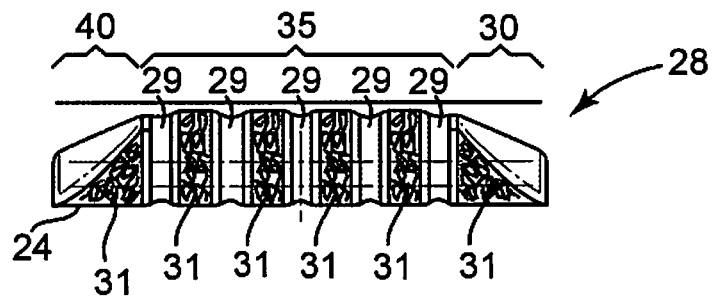
FIG. 9A is a side view of one embodiment of an abrading head of the present invention.
Figure 9B:
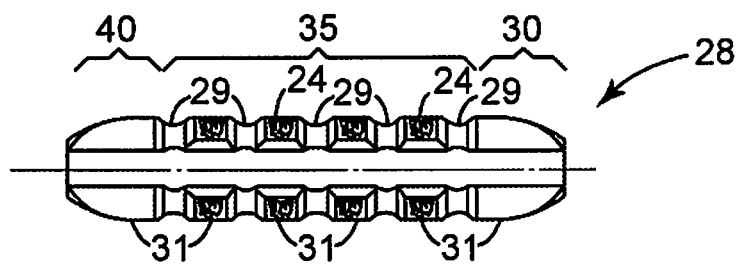
FIG. 9B is a bottom view of one embodiment of an abrading head of the present invention.
Figure 9C:
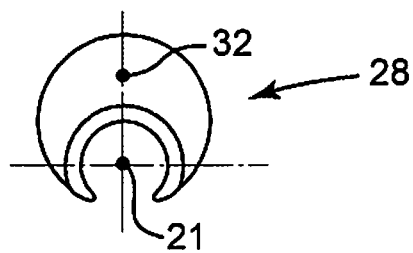
FIG. 9C is a front view of one embodiment of an abrading head of the present invention.

As best illustrated in FIGS. 6A-6C, an at least partially enclosed lumen or slot 23 may be provided longitudinally through the enlarged abrading head 28 along the rotational axis 21 of the drive shaft 20 for securing the abrading head 28 to the drive shaft 20 in a manner well known to those skilled in the art. In the embodiment shown in FIG. 6C, a hollowed section 2 is defined by the eccentric abrading head 28 and is provided to lessen the mass of the abrading head 28 to facilitate atraumatic abrasion, and improve predictability of control of the orbital pathway of the abrading head 28 during high speed, i.e., 20,000 to 200,000 rpm, operation, and/or to increase the eccentricity and asymmetry of the abrading head 28 through designed manipulation of the center of mass of the abrading head 28 relative to the rotational axis of the drive shaft as will be discussed further infra, thereby increasing the rotational diameter of the abrading head 28. Alternate embodiments of abrading head 28 may not comprise the hollowed section 2. Hollowed section 2 is not required to achieve eccentricity of the abrading head 28, comprising a center of mass that is offset from the rotational axis of the drive shaft 20.

In certain embodiments, abrading head 28 may be fixedly attached to the drive shaft 20, wherein the drive shaft comprises one single unit. Alternatively, as will be discussed below, the drive shaft 20 may comprise two separate pieces, wherein the enlarged eccentric abrading head 28 is fixedly attached to both drive shaft 20 pieces, with a gap therebetween. This two-piece drive shaft construction technique may, in combination with hollowed section 2, allow further manipulation of the placement of the center of mass of the abrading head 28. The size and shape of the hollowed section 2, when present, may be modified to optimize the orbital rotational path of the abrading head 28 for particularly desirable rotational speeds. Those skilled in the art will readily recognize the various possible configurations, each of which is within the scope of the present invention.

As will be readily recognized by the skilled artisan, at least one eccentric abrading head 28 may be attached to the drive shaft 20. One, two, three or more abrading heads 28 may be employed, each with differing geometries, profiles, number and placement of groove(s) 29, abrasive placement and other functional characteristics in order to maximize efficiency and efficacy.

The embodiment of FIGS. 5 and 6A-6C illustrates the distal 30 and proximal 40 sections being of symmetrical shape and length as well as equivalent slopes in the distal 30 and proximal sections leading up to the intermediate section 35. Alternate embodiments may increase the length of either the proximal portion 30 or the distal portion 40, to create an asymmetrical profile. In general, the symmetry of the abrading head 28 as illustrated in FIGS. 5 and 6A-6C is preferred, though alternate embodiments may comprise a larger or smaller degree of slope in distal 30 and/or proximal 40 sections. Additionally, the distal 30 and/or proximal 40 sections and/or the intermediate section 35 may have a longer or shorter length. Each such combination is within the scope of the present invention.

Because the distal 30 and proximal 40 sections are cone-shaped while the intermediate section 35 is cylindrical, the eccentric abrading head 28 of the present invention comprises a center of mass 32 that is spaced geometrically and radially away from the longitudinal rotational axis 21 of the drive shaft 20. Offsetting the center of mass 32 from the drive shaft's axis of rotation 21 provides the enlarged abrading head 28 with an eccentricity that permits it to open an artery to a diameter substantially larger during high-speed rotation than the nominal diameter of the enlarged eccentric abrading head 28. Preferably the opened diameter is at least twice as large as the nominal resting diameter of the enlarged eccentric abrading head 28. Additionally, such offsetting of the center of mass 32 may be enhanced or manipulated by varying the amount of mass and location of mass in the intermediate section 35 by, e.g., including a hollowed section 2 and varying its size, location and shape within the intermediate section 35.

It should be understood that, as used herein, the words "eccentric" and "eccentricity" are defined and used herein to refer to either a difference in location between the geometric center of the enlarged abrading head 28 and the rotational axis 21 of the drive shaft 20, or to a difference in location between the center of mass 32 of the enlarged abrading head 28 and the rotational axis 21 of the drive shaft 20. Either such difference, at the proper rotational speeds, will enable the eccentric enlarged abrading head 28 to open a stenosis to a diameter substantially greater than the nominal diameter of the eccentric enlarged abrading head 28.

The abrading head 28 of the rotational atherectomy device of the invention may be constructed of stainless steel, tungsten or similar material. The abrading head 28 may be a single piece unitary construction or, alternatively, may be an assembly of two or more abrading head components fitted and fixed together to achieve the objects of the present invention.

Turning now to FIGS. 7A-7D, another embodiment of the abrading head 28 is illustrated. This embodiment illustrates, interalia, the variation of the slope of the distal 30 and proximal 40 sections as compared with the embodiment in FIGS. 6A-6C. The embodiment in FIGS. 7A-7D comprises a smaller degree of slope in the distal 30 and proximal 30 sections relative to the intermediate section 35. This smaller degree of slope may contribute to longer distal 30 and proximal 40 sections in comparison with the embodiment of FIGS. 6A-6C. Again, axial grooves 29 are provided on the intermediate section 35 and not on the distal 30 and/or proximal 40 sections, though addition of groove(s) 29 thereon is within the scope of this invention. Abrasive material 24 may be bound to the non-grooved sections 31 located between each groove 29. Alternate embodiments may comprise the abrasive material 24 being further bound within the groove(s) 29. The center of mass 32 of the abrading head 28 is offset from the rotational axis 21 of the drive shaft 20 in this embodiment as well as in all others disclosed herein.

With reference now to FIGS. 8A-8D, the embodiment illustrated comprises relatively short distal 40 and proximal 30 sections in combination with a relatively long intermediate section 35 as compared with the embodiments discussed supra. This results in a relatively flattened configuration wherein the center of mass 32 is relatively close to the rotational axis 21 of the drive shaft 20 in comparison with that of the prior-discussed embodiments. Thus, this exemplary embodiment illustrates several of the variables that may be manipulated to maximize the efficacy of the design.

The described embodiments supra, and each variation therein, may be further carried forward into still-more alternative embodiments of the abrading head 28 as shown in FIGS. 9A-9C and 10A-10C. Specifically, in FIGS. 9A-9C, the groove(s) 29 are radial rather than axial with abrasive 24 in the non-grooved regions 31 defined between adjacent grooves 29.

Figure 10A:
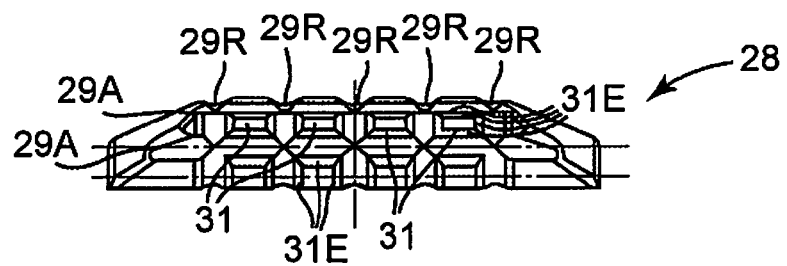
FIG. 10A is a side view of one embodiment of an abrading head of the present invention.
Figure 10B:
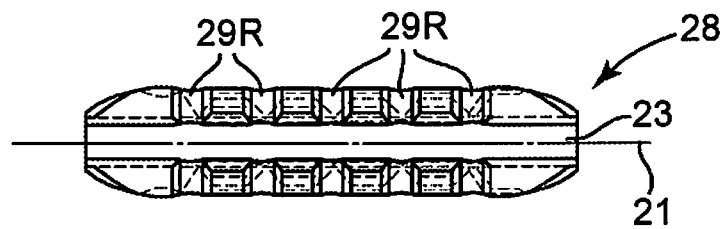
FIG. 10B is a bottom view of one embodiment of an abrading head of the present invention.
Figure 10C:
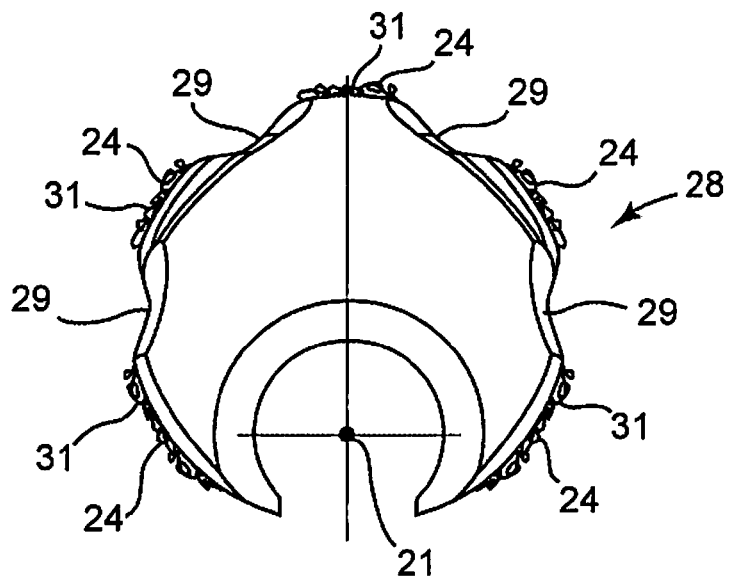
FIG. 10C is a front view of one embodiment of an abrading head of the present invention.

In FIGS. 10A-10C, an embodiment of the radial grooves 29R and axial grooves 29A intersect to form discrete non-grooved regions 31 with abrasive 24 thereon. These discrete non-grooved regions 31 may comprise, and are defined by, four edges 31E to facilitate cutting of stenotic tissue, the sharp edges 31E formed and defined by the intersection of radial grooves 29R with the axial grooves 29A on the intermediate section 35. As with other embodiments, the distal 30 and/or proximal 40 sections may comprise grooves 29 as well.

The extent to which a stenosis in an artery can be opened to a diameter larger than the nominal diameter of the enlarged abrading head 28 of the present invention depends on several parameters, including the shape of the enlarged abrading head 28, the mass of the eccentric enlarged abrading head 28, the distribution of that mass within the abrading head 28 and, therefore, the location of the center of mass 32 within the abrading head 28 with respect to the rotational axis 21 of the drive shaft 20, and the speed of rotation of the drive shaft 20 and abrading head 28 mounted thereon.

The speed of rotation of the abrading head 28 is a significant factor in determining the centrifugal force with which the tissue removing surface of the enlarged abrading head 28 is pressed against the stenotic tissue, thereby permitting the operator to control the rate of tissue removal. Control of the rotational speed also allows, to some extent, control over the maximum diameter to which the device will open a stenosis. Applicants have also found that the ability to reliably control the force with which the tissue removing surface is pressed against the stenotic tissue not only permits the operator to better control the rate of tissue removal but also provides better control of the size of the particles being removed.

Although not wishing to be constrained to any particular theory of operation, applicants believe that offsetting the center of mass 32 from the axis of rotation 21 of the drive shaft 20 produces an "orbital" movement of the enlarged abrading head 28, the diameter of the "orbit" being controllable by varying, inter alia, the rotational speed of the drive shaft 20. Applicants have empirically demonstrated that by varying the rotational speed of the drive shaft 20 one can control the centrifugal force urging the tissue removing surface of the enlarged abrading head 28 against the surface of the stenosis. The centrifugal force can be determined according to the formula:

$$F_c = m\Delta x(\pi n/30)^2$$

where $F_c$ is the centrifugal force, m is the mass of the enlarged abrading head 28, $\Delta x$ is the distance between the center of mass 32 of the enlarged abrading head 28 and the rotational axis 21 of the drive shaft 20, and n is the rotational speed in revolutions per minute (rpm). Controlling this force $F_c$ provides control over the rapidity with which tissue is removed, control over the maximum diameter to which the device will open a stenosis, and improved control over the particle size of the tissue being removed.

The abrading head 28 of the present invention may comprise more mass than typical prior art high speed atherectomy abrading devices. As a result, a larger orbit, i.e., a larger rotational diameter, may be achieved during high speed rotation which, in turn, allows for use of a smaller abrading head than with prior art devices. In addition to allowing for the creation of pilot holes in completely or substantially blocked arteries and the like, using a smaller abrading head will allow for greater ease of access and less trauma during insertion.

Operationally, using the rotational atherectomy device of the invention the eccentric enlarged abrading head 28 is repeatedly moved distally and proximally through the stenosis. By changing the rotational speed of the device he or she is able to control the force with which the tissue removal surface is pressed against the stenotic tissue, thereby being able to better control the speed of the plaque removal as well as the particle size of tissue removed. Since the stenosis is being opened to a diameter larger than the nominal diameter of the enlarged abrading head 28, the cooling solution and the blood are able to constantly flow around the enlarged abrading head. In addition, the groove(s) 29, 29R and/or 29A provide a channel(s) for fluid flow around the abrading head 28. Such constant flow of blood and cooling solution constantly flushes away removed tissue particles, thus providing uniform release of removed particles, once the abrading head 28 has passed through the lesion once.

The eccentric enlarged abrading head 28 may comprise a maximum cross-sectional diameter ranging between about 1.0 mm to about 3.0 mm. Thus, the eccentric enlarged abrading head may comprise cross-sectional diameters including, but not limited to: 1.0 mm, 1.25 mm, 1.50 mm, 1.75 mm, 2.0 mm, 2.25 mm, 2.50 mm, 2.75 mm, and 3.0 mm. Those skilled in the art will readily recognize that the incremental increases of 0.25 mm within the above-listing of cross-sectional diameter are exemplary only, the present invention is not limited by the exemplary listing and, as a result, other incremental increases in cross-sectional diameter are possible and within the scope of the present invention.

Because, as described above, the eccentricity of the enlarged abrading head 28 is dependent on a number of parameters, applicants have found that the following design parameters may be considered regarding the distance between the rotational axis 21 of the drive shaft 20 and the geometric center of a face of a transverse cross-section, taken at a position of maximum cross-sectional diameter of the eccentric enlarged abrading head: for a device having an eccentric enlarged abrading head with a maximum cross-sectional diameter between about 1.0 mm and about 1.5 mm, desirably the geometric center should be spaced away from the rotational axis of the drive shaft by a distance of at least about 0.02 mm, and preferably by a distance of at least about 0.035 mm; for a device having an eccentric enlarged abrading head with a maximum cross-sectional diameter between about 1.5 mm and about 1.75 mm, desirably the geometric center should be spaced away from the rotational axis of the drive shaft by a distance of at least about 0.05 mm, preferably by a distance of at least about 0.07 mm, and most preferably by a distance of at least about 0.09 mm; for a device having an eccentric enlarged abrading head with a maximum cross-sectional diameter between about 1.75 mm and about 2.0 mm, desirably the geometric center should be spaced away from the rotational axis of the drive shaft by a distance of at least about 0.1 mm, preferably by a distance of at least about 0.15 mm, and most preferably by a distance of at least about 0.2 mm; and for a device having an eccentric enlarged abrading head with a maximum cross-sectional diameter above 2.0 mm, desirably the geometric center should be spaced away from the rotational axis of the drive shaft by a distance of at least about 0.15 mm, preferably by a distance of at least about 0.25 mm, and most preferably by a distance of at least about 0.3 mm.

Design parameters can also be based on the location of the center of mass. For a device having an eccentric enlarged abrading head 28 with a maximum cross-sectional diameter between about 1.0 mm and about 1.5 mm, desirably the center of mass should be spaced away from the rotational axis of the drive shaft by a distance of at least about 0.013 mm, and preferably by a distance of at least about 0.02 mm; for a device having an eccentric enlarged abrading head 28 with a maximum cross-sectional diameter between about 1.5 mm and about 1.75 mm, desirably the center of mass should be spaced away from the rotational axis of the drive shaft by a distance of at least about 0.03 mm, and preferably by a distance of at least about 0.05 mm; for a device having an eccentric enlarged abrading head with a maximum cross-sectional diameter between about 1.75 mm and about 2.0 mm, desirably the center of mass should be spaced away from the rotational axis of the drive shaft by a distance of at least about 0.06 mm, and preferably by a distance of at least about 0.1 mm; and for a device having an eccentric enlarged abrading head with a maximum cross-sectional diameter above 2.0 mm, desirably the center of mass should be spaced away from the rotational axis of the drive shaft by a distance of at least about 0.1 mm, and preferably by a distance of at least about 0.16 mm.

Preferably the design parameters are selected so that the enlarged abrading head 28 is sufficiently eccentric that, when rotated over a stationary guide wire 15 (held sufficiently taut so as to preclude any substantial movement of the guide wire) at a rotational speed greater than about 20,000 rpm, at least a portion of its tissue removing surface 37 may rotate through a path (whether or not such path is perfectly regular or circular) having a diameter larger than the maximum nominal diameter of the eccentric enlarged abrading head 28. For example, and without limitation, for an enlarged abrading head 28 having a maximum diameter between about 1.5 mm and about 1.75 mm, at least a portion of the abrading head 28 may rotate through a path having a diameter at least about 10% larger than the maximum nominal diameter of the eccentric enlarged abrading head 28, preferably at least about 15% larger than the maximum nominal diameter of the eccentric enlarged abrading head 28, and most preferably at least about 20% larger than the maximum nominal diameter of the eccentric enlarged abrading head 28. For an enlarged abrading head having a maximum diameter between about 1.75 mm and about 2.0 mm, at least a portion of the abrading head 28 may rotate through a path having a diameter at least about 20% larger than the maximum nominal diameter of the eccentric enlarged abrading head 28, preferably at least about 25% larger than the maximum nominal diameter of the eccentric enlarged abrading head 28, and most preferably at least about 30% larger than the maximum nominal diameter of the eccentric enlarged abrading head 28. For an enlarged abrading head 28 having a maximum diameter of at least about 2.0 mm, at least a portion of the abrading head 28 may rotate through a path having a diameter at least about 30% larger than the maximum nominal diameter of the eccentric enlarged abrading head 28, and preferably at least about 40% larger than the maximum nominal diameter of the eccentric enlarged abrading head 28.

Preferably design parameters are selected so that the enlarged abrading head 28 is sufficiently eccentric that, when rotated over a stationary guide wire 15 at a speed between about 20,000 rpm and about 200,000 rpm, at least a portion of its abrading head 28 rotates through a path (whether or not such path is perfectly regular or circular) with a maximum diameter that is substantially larger than the maximum nominal diameter of the resting eccentric enlarged abrading head 28. In various embodiments, the present invention is capable of defining a substantially orbital path with a maximum diameter that is incrementally between at least about 50% and about 400% larger than the maximum nominal diameter of the resting eccentric enlarged abrading head 28. Desirably such orbital path comprises a maximum diameter that is between at least about 200% and about 400% larger than the maximum nominal diameter of the resting eccentric enlarged abrading head 28.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A high-speed rotational atherectomy device for opening a stenosis in an artery having a given diameter, comprising:
    a guide wire having a maximum diameter less than the diameter of the artery;
    a flexible elongated, rotatable drive shaft advanceable over the guide wire, the drive shaft having a rotational axis; and
    at least one eccentric abrading head attached to the drive shaft, the abrading head having a mass, the abrading head mass comprising a distribution, and a nominal resting diameter and comprising proximal, intermediate and distal portions, wherein the proximal portion comprises a proximal outer surface, the intermediate portion comprises an intermediate outer surface, the intermediate portion having a mass located therein, and the distal portion comprises a distal outer surface, the proximal outer surface having diameters that increase distally, the distal outer surface having diameters that decrease distally, and the intermediate outer surface being cylindrical, wherein at least the intermediate outer surface comprises at least one axial groove and at least one non-grooved section, and wherein the abrading head defines a drive shaft lumen therethrough, wherein the drive shaft at least partially traverses the drive shaft lumen,
    the at least one eccentric abrading head further comprising a geometric center location radially spaced from the drive shaft's rotational axis, a hollowed cavity within the intermediate portion, the hollowed cavity lessening the amount of mass within the intermediate portion and affecting the distribution of the amount and location of the mass of the at least one eccentric abrading head, and a center of mass spaced radially from the drive shaft's rotational axis as a consequence of both the geometric center location and the size and shape of the hollow cavity within the intermediate portion, wherein the at least one eccentric head is capable of achieving a high-speed rotational diameter that is at least twice as large as the nominal resting diameter of the eccentric abrading head.

2. The rotational atherectomy device of claim 1, wherein the at least one non-grooved section comprises abrasive coated thereon.

3. The rotational atherectomy device of claim 2, wherein the at least one groove comprises abrasive coated thereon.

4. The rotational atherectomy device of claim 1, wherein the portion of the drive shaft traversing the drive shaft lumen and attaching thereto comprises a single, unbroken drive shaft.

5. The rotational atherectomy device of claim 1, wherein the portion of the drive shaft traversing the drive shaft lumen and attaching thereto comprises at least two sections, each section attached to the drive shaft lumen with a gap between the at least two drive shaft sections.

6. The rotational atherectomy device of claim 1 wherein the eccentric enlarged diameter section has a maximum diameter between about 1.0 mm and about 1.5 mm, and the center of mass is spaced away from the rotational axis of the drive shaft by a distance of at least about 0.013 mm.

7. The rotational atherectomy device of claim 1 wherein the eccentric enlarged diameter section has a maximum diameter between about 1.5 mm and about 1.75 mm, and the center of mass is spaced away from the rotational axis of the drive shaft by a distance of at least about 0.03 mm.

8. The rotational atherectomy device of claim 1 wherein the eccentric enlarged diameter section has a maximum diameter between about 1.75 mm and about 2.0 mm, and the center of mass is spaced away from the rotational axis of the drive shaft by a distance of at least about 0.06 mm.

9. The rotational atherectomy device of claim 1 wherein the eccentric enlarged diameter section has a maximum diameter of at least about 2.0 mm, and the center of mass is spaced away from the rotational axis of the drive shaft by a distance of at least about 0.1 mm.

10. The rotational atherectomy device of claim 1 wherein the eccentric enlarged diameter section has a maximum diameter between about 1.0 mm and about 1.5 mm, and the center of mass is spaced away from the rotational axis of the drive shaft by a distance of at least about 0.02 mm.

11. The rotational atherectomy device of claim 1 wherein the eccentric enlarged diameter section has a maximum diameter between about 1.5 mm and about 1.75 mm, and the center of mass is spaced away from the rotational axis of the drive shaft by a distance of at least about 0.05 mm.

12. The rotational atherectomy device of claim 1 wherein the eccentric enlarged diameter section has a maximum diameter between about 1.75 mm and about 2.0 mm, and the center of mass is spaced away from the rotational axis of the drive shaft by a distance of at least about 0.1 mm.

13. The rotational atherectomy device of claim 1 wherein the eccentric enlarged diameter section has a maximum diameter of at least about 2.0 mm, and the center of mass is spaced away from the rotational axis of the drive shaft by a distance of at least about 0.16 mm.

14. The rotational atherectomy device of claim 1, further comprising the at least one groove having a curvilinear profile.

15. The rotational atherectomy device of claim 1, further comprising the at least one groove having a non-curvilinear profile.

* * * * *